US012656178B2

(12) United States Patent
Bischoff et al.

(10) Patent No.: US 12,656,178 B2
(45) Date of Patent: Jun. 16, 2026

(54) METHOD AND SYSTEM FOR A COLOR MATCHING PROCESS WITH A COMPENSATION OF APPLICATION PROCESS BIASES

(71) Applicant: BASF Coatings GmbH, Muenster (DE)

(72) Inventors: Guido Bischoff, Muenster (DE); Florian Steufmehl, Muenster (DE)

(73) Assignee: BASF COATINGS GMBH, Muenster (DE)

( * ) Notice: Subject to any disclaimer, the term of this patent is extended or adjusted under 35 U.S.C. 154(b) by 135 days.

(21) Appl. No.: 18/255,243

(22) PCT Filed: Dec. 7, 2021

(86) PCT No.: PCT/EP2021/084675
§ 371 (c)(1),
(2) Date: May 31, 2023

(87) PCT Pub. No.: WO2022/122775
PCT Pub. Date: Jun. 16, 2022

(65) Prior Publication Data
US 2024/0011835 A1     Jan. 11, 2024

(30) Foreign Application Priority Data

Dec. 12, 2020   (EP) ..................................... 20213634

(51) Int. Cl.
*G01J 3/46*        (2006.01)
*G01N 33/32*       (2006.01)
(52) U.S. Cl.
CPC .............. *G01J 3/463* (2013.01); *G01N 33/32* (2013.01); *G01J 2003/467* (2013.01)

(58) Field of Classification Search
CPC ..... G01J 3/463; G01J 2003/467; G01N 33/32
See application file for complete search history.

(56) References Cited

U.S. PATENT DOCUMENTS 6,100,999 A * 8/2000 Ikegami ................... H04N 1/46
                                                    358/1.9
7,804,597 B2 * 9/2010 De Haas ................. G01J 3/463
                                                    356/402

(Continued)

FOREIGN PATENT DOCUMENTS

EP         2149038 B1 *  7/2018  ................ G01J 3/46
WO      2013/092679 A1     6/2013
WO      2016/172316 A1    10/2016

OTHER PUBLICATIONS

Anonymous: "Multivariate Linear Regression : Machine Learning Medium", Aug. 23, 2017 (Aug. 23, 2017), pp. 1-6,. Xp055806540, Retrieved from the Internet: URL:https://machinelearningmedium. com/2017 /08/23/multivariate-linear-regression/ [retrieved on May 21, 2021] the whole document.

(Continued)

*Primary Examiner* — Tarifur R Chowdhury
*Assistant Examiner* — Joshua M Carlson
(74) *Attorney, Agent, or Firm* — Armstrong Teasdale LLP

(57)              ABSTRACT

Disclosed herein is a computer-implemented method for a color matching process where an offset is determined that is relieved of an application process bias. Further disclosed herein is a respective system.

14 Claims, 2 Drawing Sheets

(56)  References Cited

U.S. PATENT DOCUMENTS

| 12,148,146 | B2 * | 11/2024 | Foderaro | .................... | G06T 7/90 |
| 2007/0242877 | A1 * | 10/2007 | Peters | .................... | G06V 10/75 |
| | | | | | 382/167 |
| 2014/0242271 | A1 * | 8/2014 | Prakash | .................... | B60S 5/00 |
| | | | | | 356/73 |
| 2016/0313294 | A1 * | 10/2016 | Dattilo | .................... | G01N 33/32 |
| 2021/0201513 | A1 * | 7/2021 | Steenhoek | ............ | G01J 3/0272 |

OTHER PUBLICATIONS

International Search Report and Written Opinion for corresponding PCT/EP2021/084675, mailed Apr. 7, 2022, 12 pages.

* cited by examiner

METHOD AND SYSTEM FOR A COLOR MATCHING PROCESS WITH A COMPENSATION OF APPLICATION PROCESS BIASES

CROSS-REFERENCE TO RELATED APPLICATIONS

This application is a U.S. National Phase Application of International Patent Application No. PCT/EP2021/084675, filed Dec. 7, 2021, which claims priority to European Patent Application No. 20213634.7, filed Dec. 12, 2020, each of which is hereby incorporated by reference herein.

FIELD OF THE INVENTION

The present invention refers to a method and a system for a color matching process with a compensation of an application process bias.

BACKGROUND

Most computer-aided color matching methods are based on physical models which describe an interaction of light with scattering or absorbing media, e.g. with colorants in paint layers. Each paint layer has specific light reflectance properties due to colorants contained. Each of these colorants has specific optical properties which are expressed by respective specific optical constants/specific optical data. Physical models can predict the light reflectance properties (color) of a paint layer/paint coating based on an information about the included colorants (respectively based on information about a respective formulation) together with the corresponding specific optical properties (respectively with the corresponding specific optical constants).

The specific optical constants of colorants describe e.g. the absorption and scattering properties (or the effect flake orientation) of colorants in the context of the respective physical model, like e.g. the K/S values in the well-known "Kubelka/Munk"-model. But the reflectance properties of a paint layer do not just only depend on the formulation. It also strongly depends on the paint application process, generally how the paint was applied to its substrate.

The specific optical properties of colorants are determined based on sample data of existing letdowns/test specimen with known formulation and known reflectance data which all were applied on a substrate by a common reference paint application process. Color predictions of a physical model as well as color matching processes are always related with this reference paint application process. The specific optical constants of the colorants include the influences of the reference paint application process to the reflectance properties of the final paint layers, respectively of the final paint coatings.

Color predictions of a physical model for a different target paint application process are subject to significant systematical errors and less accurate.

An appropriate formulation for a given target color can be predicted based on the physical model with existing optical constants of available colorants and with reflectance data of the target color as input, using numerical optimization algorithms.

The resulting formulation is supposed to match the target color as good as possible on condition that it is applied with a paint application process which is equal to the reference paint application process.

Color adjustments can be computed based on a sample, e.g. an existing tinting step or a search result of a search in a formulation database. The existing sample must have been applied with the reference paint application process because the color adjustment algorithm is based on one fundamental assumption: "A respective model bias is constant for all formulations which are close to the sample formulation". As long as the adjusted formulation of a color adjustment is similar to the sample formulation the model bias is expected to be similar. Generally, the color adjustment algorithm interprets a sample offset, respectively the offset between the measured and the predicted reflectance data of a sample, as model bias. This model bias will automatically be considered/compensated within the color adjustment algorithm and leads to a modification of the adjusted formulation (example: patent EP2149038B1). But beside the model bias a real sample can also include a systematical but non-constant bias caused by (minor) differences within a respective paint application process which is also called application process bias. This application process bias will propagate into the adjusted formulation. Depending on the scale of the application process bias of the sample the color adjustment results can be significantly inaccurate.

There are several methods available to apply paint onto a substrate: Some examples of paint application processes are:

Automatic or manual spraying process, different types or configurations of spray-guns in the laboratories (labs) or body shops, different spraying lines or drying processes in the OEM (Original Equipment Manufacturer) customer sites, drawdown method in the color development labs.

Even if the same paint (same raw material) is applied in different ways the resulting colors of paint layers (paint coatings) can strongly be influenced by the respective paint application process. Reasons for changes of the colors are:

different orientations of effect flakes in the paint layer, over-spray losses of effect flakes, particularly for big effect flakes, settling of effect flakes in the paint layer, film thickness variations of the non-hiding paint layer, tinting strength variations (shearing effects or agglomerates).

That is why it is important to use one common reference paint application process for the preparation of training data (letdowns) for the computation of optical constants of colorants, respectively of specific optical data of colorants.

For manual paint application processes, e.g. with spray-guns, the resulting color depends beside the type and the configuration of the spraying device also on the individual spraying-characteristic ("fingerprint") of the sprayer. Sprayer-dependent variations within a single paint application process are typically significantly bigger for a manual paint application process than for automatic ones. A spraying profile of a manual paint application process depends on the spraying device (e.g. the type of the spray gun), the condition inside the spray booth (e.g. the air temperature or the air humidity), the configuration of the spraying device, the individual spraying-characteristic ("fingerprint") of the sprayer and on the drying process. These variations consist of a systematic part ("fingerprint") which is almost constant for one individual sprayer/spraying profile, and a statistical part.

Color matching is an iterative process. The matching process starts with a match from scratch or a search in a formulation database for a given target color.

The term "match from scratch" comprises a color matching method which manages without information about an existing sample coating as a first solution. This method is applied e.g. if no formulation database is available or if no adequate first solution is found in a formulation database. In practice the "match from scratch" method often starts with a pre-selection step of components which are expected to be in the target color. This pre-selection step is not mandatory. The "match from scratch" method/algorithm computes as a first solution one or more preliminary matching formulas for the target color. This/these preliminary matching formula(s) can be sprayed and/or adjusted in a following step.

In comparison to a "color adjustment method", where a sample coating as first solution is available which is used to improve the color prediction accuracy of the physical model (e.g. based on an approximation of the model error by an analysis of the "sample offset"), the accuracy of a "match from scratch" method is typically lower.

The first solution is typically not close enough to the target color. An adjustment of the first solution is applied where a sample offset between a predicted color and a measured color for the first solution is considered. The sample offset consists of a systematic part ("fingerprint" of sprayer) and a statistical part. If the systematic part of the sample offset is not constant, e.g. if the adjusted formulation will be sprayed by a different sprayer than the first solution (e.g. if the adjustment is computed based on a search result in a formulation database containing solutions of plenty of different sprayers with individual spraying profile), then the color adjustment result can be significantly inaccurate. The adjusted formulation is a function of the target color and the sample offset. A non-constant sample offset will propagate into the adjusted formulation.

The term "a non-constant sample offset" comprises that the offset of the adjusted formulation (after paint application) is significantly different compared to the offset of the sample.

Therefore, it is an object of the present invention to provide for a possibility to compensate for an application process bias in color adjustment methods.

SUMMARY OF THE INVENTION

The above-mentioned object is solved by the method and the system with the features of the respective independent claims. Further embodiments are presented by the following description and the respective dependent claims.

The present disclosure refers to a computer-implemented method for a color matching process wherein an offset, also called sample offset herein, is determined that is relieved of an application process bias, wherein the color matching process uses a color adjustment algorithm which comprises a color predicting model (also simply called physical model) which is implemented and running on at least one computer processor, and a database which comprises specific optical data of individual color components, the specific optical data of the individual color components being determined on the basis of known reference paint coatings with known reference color formulations and known measured reference colors, the reference paint coatings being applied on a substrate using a reference paint application process, respectively, the method comprising:

A. receiving, via at least one interface, data of a color formulation of a sample paint coating as a first solution for a target color to be matched,
   B. retrieving, from the database, specific optical data of individual color components used in the color formulation of the sample paint coating, C. receiving, via the at least one interface, a measured color of the sample paint coating applied on a substrate using a sample paint application process,
   D. calculating, using the at least one computer processor and a numerical method implemented and running on the at least one computer processor, application adaption parameters for the sample paint application process by minimizing a given cost function starting from a given set of initial application adaption parameters, and making the calculated application adaption parameters available to an application adaption module as input parameters,
   E. predicting the color of the sample paint coating for the given sample paint application process, using the color predicting model and the data of the color formulation of the sample paint coating and the retrieved specific optical data of the individual color components used in the color formulation of the sample paint coating as model input parameters, and including the calculated application adaption parameters by means of the application adaption module which interworks with the color predicting model,
   F. calculating the offset as difference between the measured color and the predicted color of the sample paint coating.

The measured color of the sample paint coating may be retrieved from a database which comprises data of measured colors of a number of paint coatings including the sample paint coating wherein the paint coatings have been previously applied onto a substrate using the sample paint application process. Alternatively, the sample paint coating may be applied on to the substrate using the sample paint application process, when carrying out the proposed method, i.e. as a further step in the proposed method, i.e. during the implementation of the proposed method.

In the scope of the present invention a sample paint application process defines a specific spraying profile which specifies a spraying device, a spraying condition, a configuration of the spraying device, individual spraying-characteristics ("fingerprint") of an individual sprayer and/or a drying process.

The terms "specific optical data of individual color components", "specific optical data of the individual color components" or "specific optical data of the colorants" are used synonymously herein and comprise specific optical properties and specific optical constants of the respective individual color components, i.e. colorants. The individual color components used in the color formulations of respective paint coatings are selected from the group comprising at least: color pigments, i.e. so-called solid pigments, effect pigments, binders, solvents and additives, such as matting pastes.

The terms "color", "color data", "reflectance", "reflectance data" and "reflectance properties" are used synonymously herein. The terms "color formulation", "paint formulation" and "formulation" are used synonymously herein. The terms "processor" and "computer processor" are used synonymously herein.

Known approaches for color formulation calculation on the basis of a radiative transfer model can be found in the literature, reference is made, for example, to "Farbenphysik für industrielle Anwendungen" of Georg A. Klein.

A basic idea of the color formulation calculation is a characterization of the specific optical data, i.e. the optical properties and/or the optical constants of all relevant individual color components, e.g. of all color pastes/colorants, on the basis of previous calibration coatings, i.e. on the basis of respective measurements of such calibration coatings. These calibration coatings correspond to existing letdowns with known formulation and known reflectance data, respectively, which all were applied by the common reference paint application process. Color predictions, using the physical model (also called herein color predicting model), as well as color matching processes are always related with this reference paint application process. The specific optical constants of the colorants include the influence of the reference paint application process to the predicted reflectance properties of the respective final paint coatings/layers.

According to the present invention, the physical model for the prediction of the reflectance properties of the sample paint coating (related with the reference paint application process), i.e. for the prediction of the color of the sample paint coating is extended with an additional application adaption module: The additional application adaption module works in interaction with the physical model and is configured to adapt the predicted reflectance data to a specific target paint application process. The additional module is configurable by input of the calculated application adaption parameters. These application adaption parameters describe differences or rather a specific transfer function between the sample paint application process in comparison to the respective reference paint application process. Examples for application adaption parameters are:

Paint layer thickness adaption: more/less thick (Applicable for non-hiding paint layers; adjust the hiding power of a paint layer)

Effect flake orientation adaption: better/worse flake orientation (Applicable for effect colors; adjust the lightness-/color-flop behavior of a paint layer)

Effectivity of solid colorants: more/less effective (Adjust the tinting strength differences of solid colorants which could be cause e.g. by shearing effects or by agglomerates)

Effectivity of effect colorants: more/less effective (Adjust differences of the reflection power of effect colorants which could be caused by over-spray losses or settling or leaving effects)

The application adaption parameters for the sample paint application process can be determined implicitly based on an analysis of existing sample coating(s) (e.g. one or more existing tinting step(s) of a color matching process) which are applied with the sample paint application process. Also a list of (one or more) existing sample coating(s) from a database (which are related with the sample paint application process, particularly with an individual human sprayer) could be used for the determination of the application adaption parameters.

Generally, the sample paint application adaption parameters are determined based on sample data of a search result of a search in a formulation database. Alternatively the sample paint application adaption parameters can be loaded from a database where paint application adaption parameters ("spraying profiles") are stored with relationship to individual sprayers. The latter option is possible if the information about the individual sprayer of a respective sample is available/given.

It is possible that the search result sample was sprayed by a first sprayer and the adjusted formulation will be sprayed by a different second sprayer. The spraying profiles of the first sprayer and the second sprayer are significantly different. This leads to a systematic error in the color adjustment algorithm which is supposed to be compensated. The application adaption module "learns" from the search result sample the individual spraying profile of the first sprayer and compensates the related application process bias within the computation of the sample offset which is used as fundamental information inside the color adjustment algorithm.

Alternatively, the paint application adaption parameters of the first sprayer (which describe his spraying profile) can also be loaded from a database which contains paint application adaption parameters corresponding to individual sprayers.

As already mentioned above, the application adaption parameters for the sample paint application process are calculated, using the numerical method that is implemented and running on the at least one computer processor. The numerical method is configured to minimize the given cost function. The numerical method and the color predicting model form part of the color adjustment algorithm.

According to one embodiment of the proposed method, the given cost function is chosen as a color distance between the measured color of a second sample paint coating which is applied on a substrate using the sample paint application process, and the predicted color of the second sample paint coating, wherein the color predicting model is used to predict the color of the second sample paint coating by using as input parameters the color formulation of the second sample paint coating and the specific optical data of the individual color components used in the color formulation of the second sample paint coating and retrieved from the database, and respective preliminary application adaption parameters resulting in the course of minimization, starting with the given set of initial application adaption parameters wherein the application adaption parameters are calculated by comparing the recursively predicted color of the second sample paint coating with the measured color of the second sample paint coating until the given cost function falls below a given threshold. The initial application adaption parameters are neutral parameters. That means that use of the initial application adaption parameters yields to color predictions which are equal to those using the reference paint application process. The given threshold can also be determined dynamically, e.g. indicating a specific state of the minimization that cannot be further improved. It is possible that the application adaption parameters are calculated by means of a plurality of second sample paint coatings, all being described by a respective color formulation and a measured color and handled as described before. Thanks to a large amount of data used, reliable application adaption parameters may be obtained.

According to a further embodiment, the sample paint coating and the second paint coating are the same. Alternatively, the sample paint coating and the second paint coating differ from each, but are applied with the same sample application adaption process.

According to a further embodiment of the proposed method, the application adaption module is configurable by direct input of specific application adaption parameters, e.g. by human input.

According to another embodiment of the proposed method, the application adaption module is configurable by loading specific application adaption parameters from a database in which application adaption parameters are stored with relationship to spraying profile ID's, e.g. to individual sprayers.

Each application adaption parameter is assigned to an adaption measure of a number of different adaption measures, the number of different adaption measures comprising at least one of: layer thickness adaption, adaption of effect flake orientation distribution, adaption of effectivity of solid color components, adaption of effectivity of effect color components.

According to a second aspect of the present invention the method further comprises the following steps:

providing a color formulation calculation algorithm, also called color adjustment algorithm, implemented and running on the at least one computer processor for determining a target color formulation for a target paint coating which matches the target color when being applied on a substrate using the reference paint application process, calculating, using the target color and the calculated offset (from a sample paint coating) as input parameters for the color formulation calculation algorithm, a color formulation with optimized concentrations of individual color components as target color formulation for the target paint coating when the target paint coating is applied on a substrate using the reference paint application process.

According to an embodiment of the proposed method, the color formulation calculation algorithm is realised by a numerical method and the color predicting model. The numerical method is configured to optimize concentrations of individual color components of a preliminary color formulation in relation to the target color by minimizing a given cost function, starting from a given initial color formulation, the given cost function being particularly chosen as a color distance between the received target color and a predicted color of the preliminary color formulation. The color predicting model is configured to predict the color of the preliminary color formulation by using as input parameters the calculated offset of the respective sample paint coating, concentrations of the individual color components used in the preliminary color formulation, specific optical data of the individual color components used in the preliminary color formulation and retrieved from the database. The optimized concentrations of the color components are calculated by comparing the recursively predicted color of the preliminary color formulation with the target color until the given cost function falls below a given threshold. Each numerical method comprises a number of successive approximation steps. In each approximation step, a preliminary color formulation is assumed/provided and fed into the physical model in order to predict its respective reflectance data, i.e. its color, which are then compared, using the cost function, with the target color. The given threshold can also be determined dynamically, e.g. indicating a specific state of the minimization that cannot be further improved.

As already indicated before, for real samples the measured reflectance data (the measured color) is always (slightly) different to the predicted reflectance data (predicted color) of the physical model ("sample offset"). Reasons for this sample offset between reality and theory are e.g.:

Model bias: because no model is 100% accurate

Application process bias: e.g. a special characteristic of a human sprayer ("fingerprint")

Statistical error of the instrument: e.g. caused by temperature

So far, a color adjustment algorithm interprets the complete sample offset as model bias and modifies an adjusted paint formulation in the way that the respective sample offset will be compensated. Here, the application process bias is part of the sample offset and expected to be constant. If the application process bias is non-constant then it acts as element of instability in the color adjustment algorithm. If e.g. the measured color of a sample is too bright because of an application process bias then the color adjustment algorithm would compute an adjusted formulation which would be too dark if it would be applied with the reference paint application process. Depending on the scale of the sample offset the color adjustment results can be significantly inaccurate because of error propagation.

The proposed method of the invention serves to eliminate such application process bias in the sample offset, herein also simply called offset. The improvement of the accuracy of the sample offset directly improves the quality/accuracy of the adjusted paint formulation. The offset of a sample between the measured color and the predicted color is analyzed regarding a potentially included application process bias in the measured color. The basic idea is to decompose the sample offset with an application adaption model into an application process part and a residual part. The residual part includes e.g. the model bias and a statistical error. The application process part is supposed to be removed from the sample offset, because it is defined to be non-constant and systematic: It represents a systematic application difference between an individual sprayer vs. the reference paint application process. The residual part of the sample offset will mainly consist of the model bias which will be correctly handled within the color adjustment algorithm, herein also called color formulation calculation algorithm.

As already mentioned above, it is possible that the search result sample was sprayed by a first sprayer and the adjusted formulation will be sprayed by a different second sprayer. The spraying profiles of the first sprayer and the second sprayer are significantly different. This leads to a systematic error in the color adjustment algorithm which is supposed to be compensated. The application adaption module "learns" from the search result sample the individual spraying profile of the first sprayer and compensates the related application process bias within the computation of the sample offset which is used as fundamental information inside the color adjustment algorithm.

Alternatively, the paint application adaption parameters of the first sprayer (which describe his spraying profile) can also be loaded from a database which contains paint application adaption parameters corresponding to individual sprayers.

The present invention also refers to a system, comprising at least:

a database which comprises individual color components, such as pigments and/or pigment classes, and specific optical data associated with the respective individual color components, the specific optical data of the individual color components being determined on the basis of known reference paint coatings with known reference color formulations and known measured reference colors, the reference paint coatings being applied to a substrate using a reference paint application process, respectively, at least one computer processor, which is in communicative connection with the database, and programmed to execute the proposed method of the invention as described herein.

The system may further comprise an input device that is configured to receive, via an appropriate interface, such as USB, an input of data. Such input device can be a computer keyboard, a microphone, a video camera, a data carrier or any combination thereof. The system may further comprise an output device that is configured to output, and in particular to display, the respective results calculated by carrying out one embodiment of the above described method. The output device is one of the group comprising at least: acoustic device, haptic device, display device and any combination thereof. The output device is in a communicative connection, via a respective interface, with the at least one computer processor.

Furthermore, the present invention refers to a non-transitory computer readable medium with a computer program with program codes that are configured and programmed, when the computer program is loaded and executed by at least one computer processor which is in communicative connection with a database which comprises individual color components, such as pigments and/or pigment classes, and specific optical data associated with the respective individual color components, the specific optical data of the individual color components being determined on the basis of known reference paint coatings with known reference color formulations and known measured reference colors, the reference paint coatings being applied to a substrate using a reference paint application process, respectively, to execute the proposed method of the invention as described herein.

Each of the communicative connections between the different components may be a direct connection or an indirect connection, respectively. Each communicative connection may be a wired or a wireless connection. Each suitable communication technology may be used. The database and the at least one computer processor, each may include one or more communications interfaces for communicating with each other. Such communication may be executed using a wired data transmission protocol, such as fiber distributed data interface (FDDI), digital subscriber line (DSL), Ethernet, asynchronous transfer mode (ATM), or any other wired transmission protocol. Alternatively, the communication may be wirelessly via wireless communication networks using any of a variety of protocols, such as General Packet Radio Service (GPRS), Universal Mobile Telecommunications System (UMTS), Code Division Multiple Access (CDMA), Long Term Evolution (LTE), wireless Universal Serial Bus (USB), and/or any other wireless protocol. The respective communication may be a combination of a wireless and a wired communication.

The computer-readable medium suitable for storing the computer program instructions (i.e. program codes) and data include all forms of non-volatile memory, media and memory devices, including by way of example semiconductor memory devices, e.g. erasable programmable read-only memory (EPROM), electrically-erasable programmable read-only memory (EEPROM), and flash memory devices; magnetic disks, such as internal hard disks or removable disks; magneto-optical disks; optical disks; CD-ROM, DVD+R, DVD-R. DVD-RAM, and DVD-ROM disks or a combination of one or more of them. Such a memory device may store various objects or data, including caches, classes, applications, backup data, jobs, web pages, web page templates, database tables, repositories storing dynamic information, and any other appropriate information including any parameters, variables, algorithms, instructions, rules, constraints, and/or references thereto. Additionally, the memory may include any other appropriate data, such as policies, logs, security or access data, reporting files, as well as others. The computer processor and the memory device can be supplemented by, or incorporated in, special purpose logic circuitry.

The computer program instructions can be a program software, a software application, a module, a software module, a script, or code, and can be written in any form of programming language, including compiled or interpreted languages, or declarative or procedural languages, and can be deployed in any form, including as a stand-alone computer program or as a module, component, subroutine, or other unit suitable for use in a computing environment. In one embodiment, the computer-executable instructions (i.e. program codes) of the present disclosure are written in HTML, TS (TypeScript), and CSS (Cascading Style Sheets).

A computer program may, but need not, correspond to a file in a respective file system. A computer program can be stored in a portion of a file that holds other programs or data, e.g., one or more scripts stored in a markup language document, in a single file dedicated to the computer program in question, or in a plurality of coordinated files, e.g., files that store one or more modules, sub-programs, or portions of code. A computer program can be deployed to be executed on one computer or on a plurality of computers that are located at one site or distributed across a plurality of sites and interconnected by a communication network. Portions of the computer programs may be designed as individual modules that implement the various features and functionality through various objects, methods, or other processes. Alternatively, the computer programs may instead include a number of sub-modules, third-party services, components, libraries, and such, as appropriate. Conversely, the features and functionality of various components can be combined into single components as appropriate.

Systems suitable for the execution of the method of the present disclosure can be based on general or special purpose microprocessors, both, or any other kind of CPU. Generally, a CPU will receive instructions and data from a read-only memory (ROM) or a random access memory (RAM) or both. Essential elements of the system are a CPU for performing or executing instructions (i.e. program codes) and one or more memory devices (such as the database) for storing instructions (i.e. program codes) and data. Generally, the system includes, or is operatively coupled to at least one memory device and is configured to receive data from or transfer data to, or both, the at least one memory device for storing data. The at least one memory device may comprise, e.g., magnetic, magneto-optical disks, or optical disks. However, the system itself need not have such memory devices. Moreover, the system can be embedded in another device, e.g., a mobile telephone, a personal digital assistant (PDA), or a portable storage device, e.g., a universal serial bus (USB) flash drive, to name just a few.

The following description is presented and provided in the context of one or more particular implementations. Various modifications to the disclosed implementations will be readily apparent to a person skilled in the art, and the general principles defined herein may be applied to other implementations and applications without departing from the scope of the disclosure.

Implementations of the subject matter and the functional operations described in the present disclosure can be implemented in digital electronic circuitry, in tangibly-embodied computer software, in computer hardware, including the structures disclosed in this disclosure and their structural equivalents, or in combinations of one or more of them. Implementations of the subject matter described in this disclosure can be implemented as one or more computer programs, i.e., one or more modules of computer program instructions encoded on a tangible, non-transitory computer-readable medium for execution by, or to control the operation of, data processing apparatus. Alternatively or in addition, the computer program instructions can be encoded on an artificially-generated propagated signal, e.g., a machine-generated electrical, optical, or electromagnetic signal that is generated to encode information for transmission to a suitable receiver device for execution by at least one computer processor. The computer-storage medium can be a machine-readable storage device, a machine-readable storage substrate, a random or serial access memory device, or a combination of one or more of them.

The details of one or more implementations of the subject matter of this specification are set forth in the accompanying drawings and the description. Other features, aspects, and advantages of the subject matter will become apparent from the description, the drawings, and the claims.

DETAILED DESCRIPTION OF THE DRAWINGS

Identical units or components are provided with identical reference signs across all figures.

Figure 1:
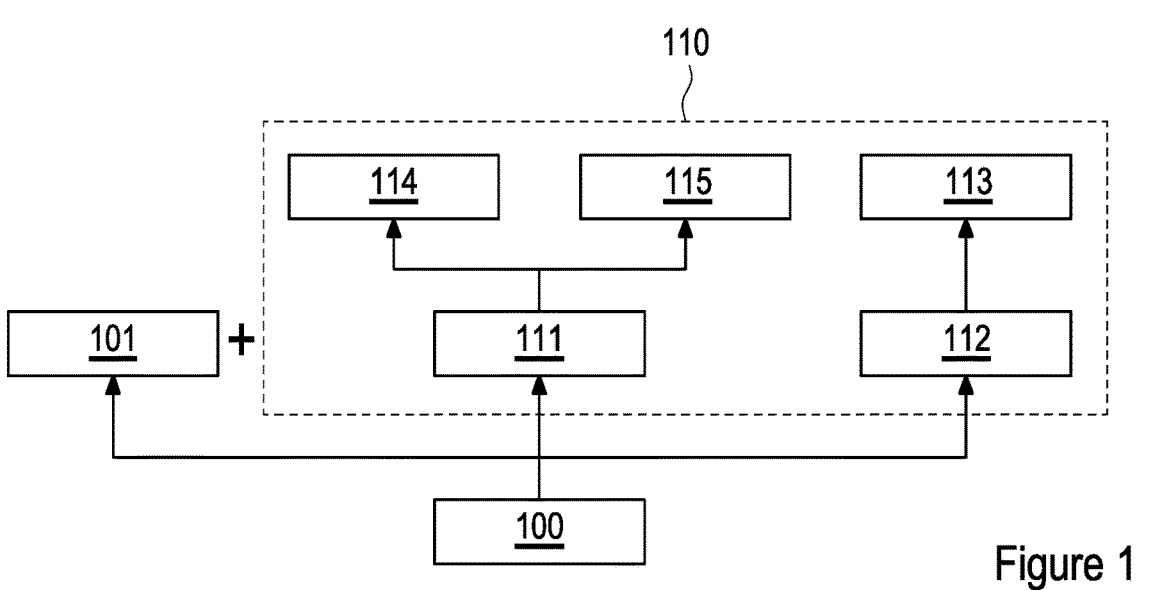
FIG. 1 shows a schematic block diagram that illustrates an embodiment of a method for providing a sample offset for a color matching process according to the present invention.

FIG. 1 shows a schematic block diagram that illustrates an offset which must be cleared of an application process bias according to an embodiment of a method according to the present invention. For real samples a measured sample color 100 is always (slightly) different to a predicted sample color which has been predicted, using a physical model. The measured sample color 100 can be expressed as a combination of a true color 101 and an offset 110. The offset 110, also called sample offset 110, corresponds to a difference between the measured sample color 100 and a predicted sample color. Reasons for this sample offset 110 between reality (measurement) and theory (physical model) are e.g.:

Model bias 114: No model is 100% accurate

Application process bias 115: i.e. how the sample has been applied onto a substrate when the sample color is measured, e.g. a special characteristic of a human sprayer ("fingerprint")

Statistical error 112 of an instrument 113, i.e. the application instrument, such as a spray gun: e.g. caused by temperature So far, a color adjustment algorithm, i.e. a paint color formulation calculation algorithm interprets the complete sample offset 110 as model bias and modifies an adjusted paint formulation in the way that the respective sample offset 110 will be compensated. That means that the application process bias 115 is part of the sample offset 110. If the application process bias 115 is non-constant, e.g. in the case of different human sprayers, then it acts as element of instability. If e.g. the measured color 100 of a sample is too bright because of an application process bias 115 then the color adjustment algorithm would compute an adjusted formulation which would be too dark if it would be applied with a respective reference paint application process. Depending on the scale of the sample offset 110 the color adjustment results can be significantly inaccurate because of error propagation.

The proposed method of the invention serves to eliminate such application process bias 115 in the sample offset 110, herein also simply called offset 110. The improvement of the accuracy of the sample offset 110 directly improves the quality/accuracy of the adjusted paint formulation. The offset 110 of a sample between the measured color 100 and the predicted color is analyzed regarding a potentially included application process bias 115 in the measured color 100. As mentioned before, the offset 110 comprises a systematical bias 111 and a statistical bias 112, also called statistical error 112. The statistical bias 112 is caused by an instrument 113, such as a sprayer gun. The systematical bias 111 comprises the model bias 114 (which is expected to be constant) and the application process bias 115 (which could be non-constant). A basic idea of the proposed method is to decompose the sample offset 110 with an application adaption module into an application process bias 115 and a residual part which comprises the model bias 114 and the statistical bias 112. The application process bias 115 is supposed to be removed from the sample offset 110, because it is defined to be non-constant. The residual part of the sample offset 110 will mainly consist of the model bias 114 which will be correctly handled within the color adjustment algorithm.

Figure 2:
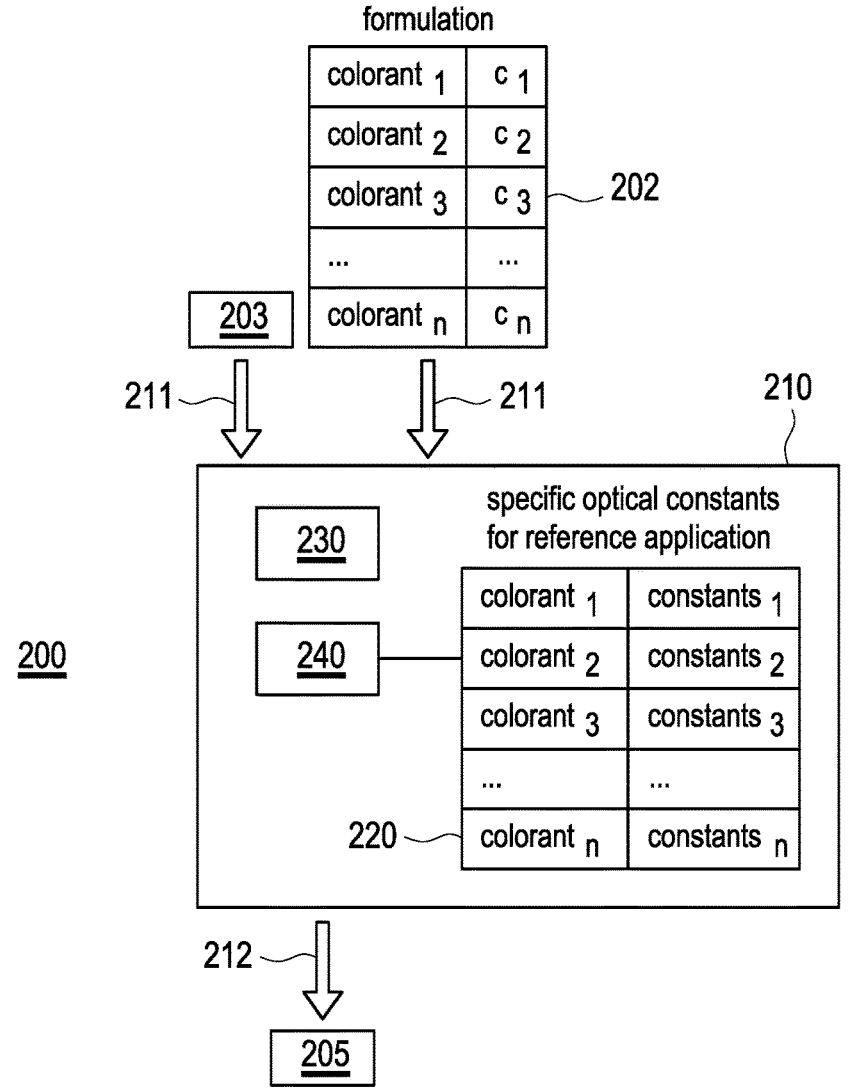
FIG. 2 shows a schematic block diagram that illustrates another embodiment of a method to compensate for an application process bias according to the present invention.

FIG. 2 shows an embodiment of a system 200 according to the present invention. The system comprises a computer processor 210 and a database 220. The database 220 comprises individual color components, $colorant_1$, $colorant_2$, $colorant_3$, . . . , $colorant_n$, such as pigments and/or pigment classes, and specific optical data, $constants_1$, $constants_2$, $constants_3$, . . . , $constants_n$, associated with the respective individual color components, the specific optical data of the individual color components being determined on the basis of known reference paint coatings with known reference color formulations and known measured reference colors, the reference paint coatings being applied onto a substrate using a common reference paint application process, respectively. The computer processor 210 is in communicative connection with the database 220, and programmed to execute an embodiment of the method as described herein.

In order to relieve a sample offset 110 from an application process bias 115 which is assigned to a sample paint application process, it is proposed to determine a difference between a measured color of a respective sample coating which is applied onto a substrate using the sample paint application process, and a predicted color of the respective sample coating which is determined using a physical model 240. Therefore, it is essential to consider the sample paint application process when making predictions using the physical model, because the actual physical model 240 is based on the assumption of using the reference paint application process and uses the database 220 which comprises the specific optical properties of colorants which are determined based on data of existing letdowns/test specimen with known formulation and known reflectance data which all were applied on a substrate by the common reference paint application process. A consideration of the sample paint application process is achieved by determining sample application adaption parameters as further input parameters of the physical model 240. These sample application adaption parameters are computed based on data of existing tinting steps, respectively of existing sample paint coatings.

These sample paint coatings are applied on a substrate using the sample paint application process. The respective sample colors 203 of the sample paint coatings are measured. Data of the respective color formulations 202 of the respective sample paint coatings are provided, wherein a respective color formulation 202 specifies all included colorants, colorant$_1$, colorant$_2$, colorant$_3$, . . . colorant$_n$ with their respective concentrations, $c_1$, $c_2$, $c_3$, . . . , $c_n$.

The data of the color formulations 202 of the sample paint coatings are received via at least one interface 211 of the computer processor 210. Furthermore, the measured colors 203 of the sample paint coatings are received via the at least one interface 211 of the computer processor 210.

A numerical method 230 and the physical model 240 are provided and implemented on the computer processor 210. The numerical method 230 is configured to optimize application adaption parameters by minimizing a given cost function starting from a given set of initial application adaption parameters. The initial application adaption parameters are neutral parameters. That means that use of the initial application adaption parameters yields to color predictions which are equal to those using the reference paint application process. The given cost function is chosen as a color distance between the measured color 203 of a respective one of the existing sample paint coatings and a predicted color of the respective sample paint coating. The physical model 240 is configured to predict the color of the respective sample paint coating by using as input parameters the color formulation 202 of the respective sample paint coating, specific optical data of the individual color components used in the color formulation 202 of the respective sample paint coating, and respective preliminary application adaption parameters resulting in the course of optimization. The specific optical data are retrieved from the database 220. The specific optical properties of colorants are determined based on data of existing letdowns/test specimen with known formulation and known reflectance data which all were applied on a substrate by the common reference paint application process. Therefore, color predictions of the physical model 240 are related with this reference paint application method. The specific optical constants/data of the colorants include the influences of the reference paint application process to the reflectance properties of the final paint layers.

By using the computer processor 210 and using the numerical method 230 and the physical model 240 implemented and running on the computer processor 210, the application adaption parameters 205 are calculated by comparing the recursively predicted color of the respective sample paint coating with the measured color 203 of the respective sample paint coating until the given cost function falls below a given threshold. The given threshold can also be determined dynamically, e.g. indicating a specific state of the minimization that cannot be further improved.

Figure 3:
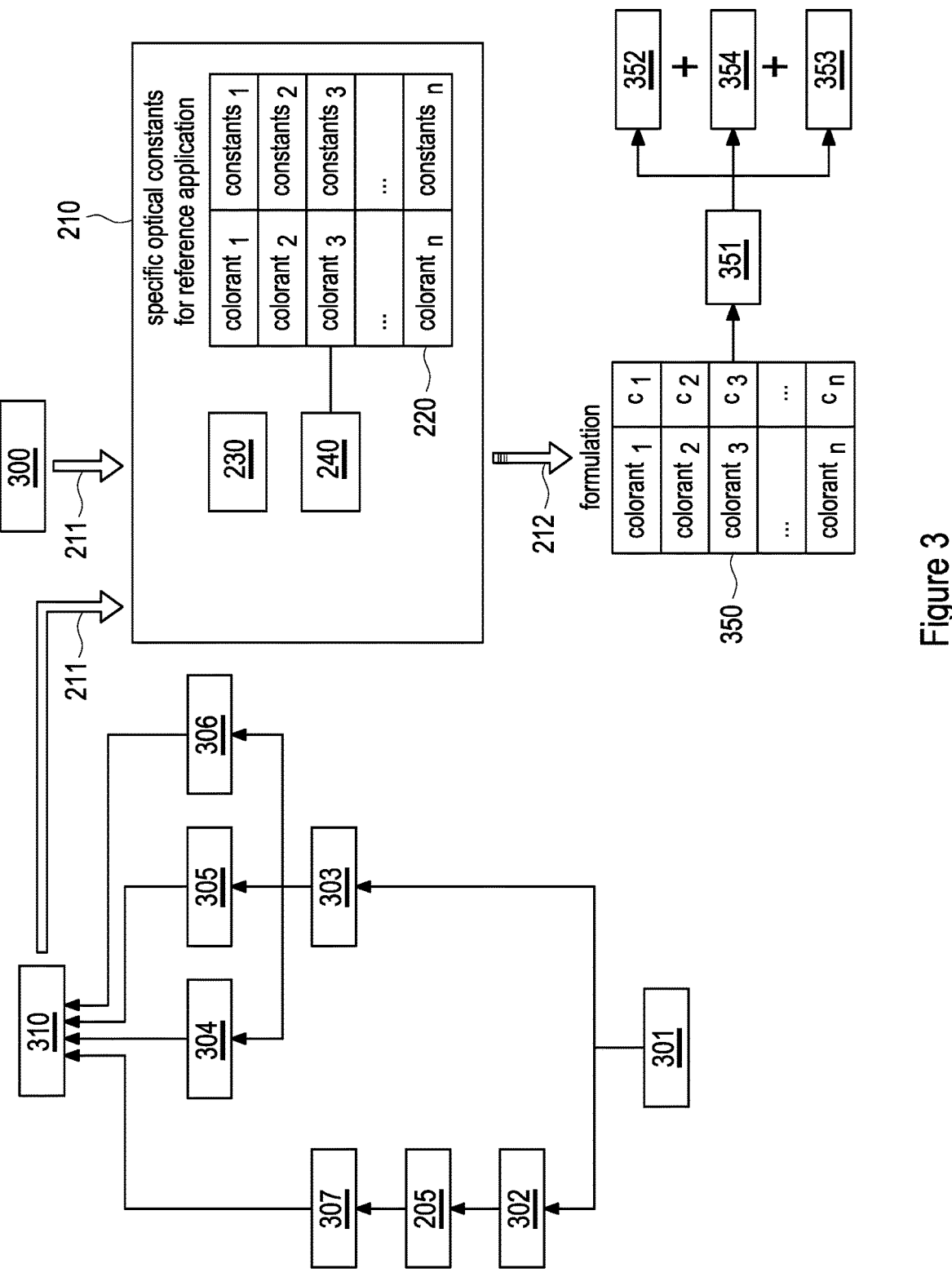
FIG. 3 shows a schematic block diagram that illustrates a further embodiment of a method for color matching according to the present invention.

The calculated optimized application adaption parameters 205 are made available and optionally output via a further interface 212 on an output device such as a display. These calculated optimized application adaption parameters 205 are characteristic for the sample paint application process. The application adaption parameters 205 are used as input parameters for the physical model 240 when determining the sample offset as a difference between a measured sample color and a predicted sample color of a first solution in a color adjustment method as illustrated in FIG. 3. By using the application adaption parameters 205, both the measured sample color and the predicted sample color are related to the same sample paint application process. Therefore, the difference between the measured sample color and the predicted sample color is rid of the influence of the sample paint application process.

A color adjustment process for a given target color 300 starts with a sample 301, e.g. an existing tinting step or a search result of a search in a formulation database as a first solution. So far, the existing sample must have been applied with the reference paint application process because the color adjustment algorithm is based on the assumption that a model bias is constant for all formulations which are close to the sample formulation. However, as already explained above, real samples or sample coatings are generally not applied with the reference paint application process, but with a sample paint application process which causes a contribution to the systematical bias of the sample offset. If this contribution of the sample paint application process to the sample offset is not considered, results of the color adjustment process will be significantly inaccurate.

The first solution 301 is typically not close enough to the target color 300. An adjustment of the first solution 301 is applied where an offset 310 between the predicted reflectance data 306 and the measured reflectance data 303 for the first solution 301 is considered.

So the adjusted formulation is a function of the target color 300 and the offset 310 between the predicted reflectance data 306 and the measured reflectance data 303 of the first solution 301. If the measured reflectance data 303 of the first solution 301 includes a bias caused by variations within the paint application process then this error will propagate into the following formulation within the iterative color matching process.

Therefore, it is proposed to avoid such paint application process bias 115 by taking into account the diversity of the paint application processes already in the first iteration step, i.e. when considering the first solution 301.

The offset 310 which is independent of the paint application process is calculated on the basis of the first solution 301. A sample formulation 302 of the first solution 301 is known. The first solution 301 is applied as paint coating on a substrate using a sample paint application process and its color is measured. The measured color 303 of the first solution 301 is provided. The measured color 303 comprises a true color 304, a systematical bias 305 and a statistical error 306. Furthermore, the physical model 240 is used to predict the color of the first solution 301 on the basis of the known formulation 302. As the physical model 240 uses the database 220 and is, thus, related to the reference paint application process, the sample paint application process is taken into account by combining the physical model 240 with the sample application adaption parameters 205 which are determined as explained in FIG. 2. The predicted color 307 of the first solution 301 is now predicted on the assumption that the underlying formulation 302 is applied as paint coating on a substrate using the sample paint application process. Therefore, both the measured color 303 and the predicted color 307 refer to the same sample paint application process. The offset 310 as difference between the measured color 303 and the predicted color 307 is, therefore, independent of the underlying sample paint application process. This offset 310 can now be used for the iterative color adjustment process.

As the first solution 301 is typically not close enough to the target color 300, the physical model 240 is used in combination with the numerical optimization algorithm 230 to obtain an optimised formulation 350 by iteration. The optimized formulation 350 specifies all included colorants, colorant$_1$, colorant$_2$, colorant$_3$, . . . colorant$_n$ with their respective concentrations, $c_1$, $c_2$, $c_3$, . . . , $c_n$. The physical model 240 uses again the database 220 as a basis for the color prediction. The target color 300 and the calculated offset 310 are used in combination in order to account for the model bias and the statistical error. Both are assumed to be similar for the sample and the formulation for the target color 300.

The target color 300 and the offset 310 are received by the computer processor 210, on which the physical model 240 and the numerical optimization algorithm 230 are implemented and running, via an interface 211. In order to determine the formulation 350 for a paint coating whose color matches the target color 300 when being applied on a substrate using the reference paint application process, the target color 300, the offset 310 and the specific optical constants of the available colorants from the database 220 are used and an optimized formulation 350 is iteratively determined. This formulation 350 and its predicted color 351 when being applied using the reference paint application process, can be output via an interface 212 on an output device. The predicted color 351 is composed of a true color 352 of the optimized formulation 350 when being applied on a substrate using the reference paint application process, and a statistical error of sample 353. Due to the inclusion of the offset 310 which is relieved of the sample application bias 115, there is no sample paint application process bias 354 any more.

LIST OF REFERENCE SIGNS 100 measured sample color
101 true color
110 offset
111 systematical bias
112 statistical error, statistical bias
113 instrument
114 model bias
115 application process bias
200 system
202 color formulation
203 measured color
205 sample application adaption parameters
210 computer processor
211 (input) interface
212 (output) interface
220 database
230 numerical optimization algorithm
240 physical model
300 target color
301 sample, sample coating
302 sample formulation
303 measured sample color
304 true color
305 systematical bias
306 statistical error
307 predicted sample color (for sample paint application process)
310 sample application adaption parameters
350 optimized formulation
351 predicted color for reference paint application process
352 true color
353 statistical error of sample
354 application process bias of sample

The invention claimed is:

1. A computer-implemented method for color matching, the method implemented by a computing system including at least one computer processor communicatively coupled to a database storing specific optical data of individual color components, wherein the specific optical data of the individual color components have been determined on the basis of known reference paint coatings with known reference color formulations and known measured reference colors, and wherein the reference paint coatings have been applied on a substrate using a reference paint application process, the method comprising:

A. receiving, via at least one interface of the at least one computer processor, data of a color formulation of a sample paint coating as a first solution for a target color to be matched, B. retrieving, from the database, specific optical data of individual color components used in the color formulation of the sample paint coating, C. receiving, via the at least one interface, a measured color of the sample paint coating applied on a substrate using a sample paint application process, D. calculating, using the at least one computer processor and a numerical method implemented and running on the at least one computer processor, application adaption parameters for the sample paint application process by minimizing a given cost function starting from a given set of initial application adaption parameters, wherein the given cost function is chosen as a color distance between a measured color of a second sample paint coating, wherein the second sample paint coating has been applied on a substrate using the sample paint application process, and a predicted color of the second sample paint coating, E. executing, on the at least one computer processor, a color predicting model trained to output a prediction of the color of the sample paint coating for the sample paint application process using the calculated application adaption parameters, the data of the color formulation of the sample paint coating, and the retrieved specific optical data of the individual color components used in the color formulation of the sample paint coating as model input parameters, F. setting as an offset a difference between the measured color and the predicted color of the sample paint coating, the offset independent of a paint application process of the sample coating and thereby eliminating an application process bias of the color predicting model, and G. applying, by the at least one computer processor, the offset to the target color to achieve, as an output from said applying, an optimized color formulation for a target paint coating having the target color independent of a paint application process of the target paint coating.

2. The method according to claim 1 wherein the color predicting model is used to predict the color of the second sample paint coating by using as input parameters a color formulation of the second sample paint coating and specific optical data of the individual color components used in the color formulation of the second sample paint coating and retrieved from the database, and respective preliminary application adaption parameters resulting in the course of minimization, starting with the given set of initial application adaption parameters, wherein the application adaption parameters are calculated by comparing a recursively predicted color of the second sample paint coating with the measured color of the second sample paint coating until the given cost function falls below a given threshold.

3. The method according to claim 2, wherein the sample paint coating and the second sample paint coating are the same.

4. The method according to claim 1, wherein the color predicting model is configurable by input of specific application adaption parameters.

5. The method according to claim 1, wherein each application adaption parameter is assigned to an adaption measure of a number of different adaption measures, the number of different adaption measures comprising at least one of: layer thickness adaption, adaption of effect flake orientation distribution, adaption of effectivity of solid color components, adaption of effectivity of effect color components, and/or adaption of individual characteristics of a human sprayer.

6. The method according to claim 1 wherein said applying the offset comprises:

calculating, by iterative executing a color formulation calculation algorithm with the offset, the optimized color formulation with optimized concentrations of individual color components as the target color formulation for the target paint coating.

7. The method according to claim 6, wherein the color formulation calculation algorithm is realised by a numerical method and the color predicting model, wherein the numerical method is configured to optimize concentrations of individual color components of a preliminary color formulation in relation to the target color by minimizing a given cost function, starting from a given initial color formulation, and the color predicting model is configured to predict the color of the preliminary color formulation by using as input parameters the calculated offset, concentrations of the individual color components used in the preliminary color formulation, specific optical data of the individual color components used in the preliminary color formulation and retrieved from the database, and wherein the optimized concentrations of the color components are calculated by comparing a recursively predicted color of the preliminary color formulation with the target color until the given cost function falls below a given threshold.

8. A system, comprising at least:

a database which comprises individual color components and specific optical data associated with the respective individual color components, the specific optical data of the individual color components being determined on the basis of known reference paint coatings with known reference color formulations and known measured reference colors, the reference paint coatings being applied on a substrate using a reference paint application process, respectively, and at least one computer processor, which is in communicative connection with the database, and programmed to execute the method according to claim 1.

9. A non-transitory computer readable medium with a computer program with program codes that are configured and programmed, when the computer program is loaded and executed by at least one computer processor which is in communicative connection with a database which comprises individual color components and specific optical data associated with the respective individual color components, the specific optical data of the individual color components being determined on the basis of known reference paint coatings with known reference color formulations and known measured reference colors, the reference paint coatings being applied on a substrate using a reference paint application process, respectively, to execute the method according claim 1.

10. The method according to claim 6, wherein the color formulation calculation algorithm is realised by a numerical method and the color predicting model, wherein the numerical method is configured to optimize concentrations of individual color components of a preliminary color formulation in relation to the target color by minimizing a given cost function, starting from a given initial color formulation, the given cost function being chosen as a color distance between the received target color and a predicted color of the preliminary color formulation, and the color predicting model is configured to predict the color of the preliminary color formulation by using as input parameters the calculated offset, concentrations of the individual color components used in the preliminary color formulation, specific optical data of the individual color components used in the preliminary color formulation and retrieved from the database, and wherein the optimized concentrations of the color components are calculated by comparing a recursively predicted color of the preliminary color formulation with the target color until the given cost function falls below a given threshold.

11. The system according to claim 8, wherein the individual color components comprise pigments and/or pigment classes.

12. The non-transitory computer readable medium according to claim 9, wherein the individual color components comprise pigments and/or pigment classes.

13. The method according to claim 2, further comprising dynamically determining the given threshold by determining a state of the given cost function cannot be further minimized.

14. The method according to claim 1, wherein the color predicting model is trained to use recursion to predict the color of the sample paint coating for the sample paint application process.

* * * * *